United States Patent [19]
Fischetti et al.

[11] Patent Number: 6,017,528
[45] Date of Patent: Jan. 25, 2000

[54] THERAPEUTIC TREATMENT OF GROUP A STREPTOCOCCAL INFECTIONS

[75] Inventors: Vincent Fischetti, West Hempstead, N.Y.; Lawrence Loomis, Columbia, Md.

[73] Assignee: New Horizons Diagnostics, Columbia, Md.

[21] Appl. No.: 09/257,025

[22] Filed: Feb. 25, 1999

Related U.S. Application Data

[63] Continuation-in-part of application No. 08/962,523, Oct. 31, 1997.

[51] Int. Cl.[7] .................................................. A61K 38/00
[52] U.S. Cl. ..................... 424/94.1; 424/440; 424/451; 424/464; 424/489; 424/45; 424/48; 514/2; 514/937; 514/944; 514/948
[58] Field of Search ........................... 424/45, 94.1, 440, 424/451, 464, 489, 48; 514/2, 937, 944, 948

*Primary Examiner*—Raj Bawa

[57] ABSTRACT

The present invention relates to compositions containing Group C streptococcal phage associated lysin enzyme for the prophylactic and therapeutic treatment of Streptococcal infections, including the infection commonly known as strep throat. Methods for therapeutically and prophylactically treating such infections also are described.

28 Claims, No Drawings

THERAPEUTIC TREATMENT OF GROUP A STREPTOCOCCAL INFECTIONS

The following application is a continuation-in-part of U.S. patent application Ser. No. 08/962,523, filed Oct. 31, 1997.

DESCRIPTION

BACKGROUND OF THE INVENTION

1. Field of the Invention

The present invention relates to a composition containing Group C Streptococcal phage associated lysin enzyme and a carrier for delivering the Group C Streptococcal phage associated lysin enzyme to the mouth, throat or nasal passages of a mammal. The composition is particularly useful for the prophylactic and therapeutic treatment of Streptococcal infections, including the infection commonly known as strep throat.

2. Description of the Prior Art

Group A streptococci have been shown to be an important pathogen capable of existing both in a carrier state in an asymptomatic individual and in a symptomatic individual with symptoms of disease ranging from a mild sore throat, tonsillitis, or impetigo. If untreated, these streptococcal infections could lead to glomerulonephritis, rheumatic fever and possibly permanent rheumatic heart disease. With the advent of antimicrobial agents, specifically penicillin derived antibiotics, the causative organism can be readily eliminated following the prescribed regimen of appropriate antibiotic therapy.

The fact that an infected individual (usually children & young adults) can pass group A streptococcal organisms to others, particularly in daycare centers and schools, necessitates the isolation of the known infected individual away from these environments for at least 24 to 72 hours after antimicrobial therapy has been initiated. It has been shown in controlled studies that early detection and appropriate treatment results in a reduction in the overall pattern of cyclic transmission of the troublesome pathogen, as well as a reduction or elimination of the sequelae of group A infections (rheumatic fever or nephritis).

U.S. Pat. No. 5,604,109 (Fischetti et al.) teaches the rapid and sensitive detection of Group A streptococcal antigens by a diagnostic assay which utilizes Group C streptococcal phage associated lysin enzyme. Such an assay can assist in rapidly identifying infected individuals, who then can receive conventional antibiotic therapy.

However, the problem of effectively combating streptococcus infections remains a problem. Patients with a streptococcal pharyngitis are highly infectious and are able to transmit the organism to close contacts resulting in an epidemic of strep throat. This is a particular problem in a school population and in the military, where people are in close proximity with one another. Moreover, there is a need for prophylactic methods of preventing streptococcal infections, because prophylactic use of antibiotics generally is not advisable for many reasons.

SUMMARY OF THE INVENTION

The present invention (which incorporates U.S. Pat. No. 5,604,109 in its entirety by reference) provides compositions containing Group C Streptococcal phage associated lysin enzyme and a carrier for delivering the Group C Streptococcal phage associated lysin enzyme to the mouth, throat or nasal passage of an animal such as a human. Such compositions can be particularly useful either as a prophylactic treatment for preventing infection following exposure to others who are infected, or as a therapeutic treatment of Streptococcal A throat infections for those who are already infected, thereby alleviating the infection.

The presence of the lysin in an oral or nasal cavity at the time when streptococci are introduced from an infected individual thus results in the killing of at least some of the incoming streptococci, thereby providing a prophylactic effect by preventing infection. This rapid and specific (lethal) activity of the lysin enzyme against an existing streptococcus infection will have a therapeutic effect by reducing the infection and helping to decrease the spread of the strep to other individuals.

In one embodiment of the invention, the lysin enzyme is administered in the form of a candy, chewing gum, lozenge, troche, tablet, a powder, an aerosol, a liquid (e.g., gargle) or a liquid spray. In another embodiment of the invention, the lysin enzyme is administered in the form of a nasal spray.

The method for the treatment of streptococcus A exposure comprises applying an effective dosage of a pharmaceutically acceptable amount of Group C streptococcal phage associated lysin enzyme to the oral or nasal mucosa of a mammal in need of treatment, permitting the lysin enzyme to remain in contact with the oral mucosa for a period of time necessary for the lysin enzyme to saturate the oral mucosa; and applying additional dosages of such the lysin enzyme in like fashion until treatment is complete. The enzyme may be administered to the mucosal lining of the throat, or of the nose, for the infection, depending on the carrier containing the lysin enzyme.

While this composition is likewise effective against group A strep infections, it may also be used against group C infections. The enzyme is likewise effective against group E streptococci.

DETAILED DESCRIPTION OF THE INVENTION

It has been discovered that the presence of the lysin in an oral cavity at the time when streptococci are introduced from an infected individual results in the killing of the incoming streptococci, thus preventing infection and providing a prophylactic treatment for preventing strep infection. This rapid and specific (lethal) activity of the lysin enzyme against streptococcus also produces a therapeutic effect in infected individuals by reducing the infection and decreasing the spread of the strep to other individuals.

The amidase muralytic (lysin) enzyme produced by the group C streptococcal organism after being infected with a particular bacteriophage (identified as C1) is isolated and harvested as is described in U.S. patent application Ser. No. 5,604,109. This Group C streptococcal enzyme, (also known as a lysin enzyme) which has unique specificity for the cell wall of groups A, C, and E Streptococci, may alternatively be isolated and harvested by any other known means.

The composition which may be used for the prophylactic and therapeutic treatment of a strep infection includes the lysin enzyme and a means of application, (such as a carrier system or an oral delivery mode) for the mucosa lining of the oral or nasal cavity.

Prior to, or at the time the enzyme is put in the carrier system or oral delivery mode, it is preferred that the enzyme be in a stabilizing buffer environment for maintaining a pH range between about 4.0 and about 8.0, more preferably between about 5.5 and about 7.5 and most preferably at about 6.1.

The stabilizing buffer should allow for the optimum activity of the lysin enzyme. The buffer may be a reducing agent, such as dithiothreitol. The stabilizing buffer may also be or include a metal chelating agent, such as ethylenediaminetetracetic acid disodium salt, or it may also contain a phosphate or citrate-phosphate buffer.

To prevent spoilage, the stabilizing buffer may further contain a bactericidal or bacteriostatic agent as a preservative, such as a small amount of sodium benzoate.

Means of application include, but are not limited to direct, indirect, carrier and special means or any combination of means. Direct application of the lysin enzyme to the nasal membranes may be by nasal sprays, nasal drops, nasal ointments, nasal washes, nasal injections, nasal packings or through the use of ointments applied to the nasal nares, the bridge of the nose, or the face or any combination of these and similar methods of application, or other known nasal carriers. Application to the mouth and throat may be made by use of throat lozenges, or through use of mouthwashes, gargles, solutions, sprays, candy, gum, etc. Thus, forms in which the lysin enzyme may be administered include but are not limited to lozenges, troches, candies, injectants, chewing gums, tablets, powders, sprays, liquids, ointments, and aerosols.

The lozenge, tablet, or gum into which the lysin enzyme is added may contain sugar, corn syrup, a variety of dyes, non-sugar sweeteners, flavorings, any binders, or combinations thereof. Similarly, any gum based products may contain acacia, carnauba wax, citric acid, corn starch, food colorings, flavorings, non-sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the invention, sugar substitutes are used in place of dextrose, sucrose, or other sugars.

The enzyme may also be placed in a nasal spray, wherein the nasal spray is the carrier. The nasal spray can be a long acting or timed release spray, and can be manufactured by means well known in the art.

Any of the carriers for the lysin enzyme may be manufactured by conventional means. However, it is preferred that any mouthwash or similar type products not contain alcohol to prevent denaturing of the enzyme. Similarly, when the lysin enzyme is being placed in a cough drop, gum, candy or lozenge during the manufacturing process, such placement should be made prior to the hardening of the lozenge or candy but after the cough drop or candy has cooled somewhat, to avoid heat denaturation of the enzyme.

The enzyme may be added to these substances in a liquid form or in a lyophilized state, whereupon it will be solubilized when it meets a liquid body. The enzyme may also be, for example, in a micelle or liposome, or some other encapsulated form, or administered as a prodrug or in an extended release form to provide a prolonged storage and/or delivery effect.

The effective dosage rates or amounts of the lysin enzyme to treat the infection will depend in part on whether the lysin will be used therapeutically or prophylactically, the duration of exposure of the recipient to the Streptococci, and/or the nature of the infection, the size and weight of the individual, etc. Determining appropriate dosage rates will be within the skill of the artisan. The duration for use of the composition containing the enzyme also depends on whether the use is for prophylactic purposes, wherein the use may be, for example, daily or weekly, for a defined time period e.g., for a week month or longer, or whether the use will be for therapeutic purposes, wherein a more intensive regimen of the use of the composition likely would be employed for a period of, for example, 2, 3, 4, 5, 6, 7, 10, or 14 days, or longer. Thus, therapeutic treatments could span several days or weeks, likely on a daily basis, and possibly at multiple intervals during the day.

In order to be effective, the enzyme should be present in an amount sufficient to provide an effective number of enzyme units in contact with the mouth, throat or nasal passage. Having too few enzyme units in contact with the mouth, throat or nasal passage, even over a long period of time, will not produce as beneficial an effect as desired. Hence, any dosage form employed should provide for an approximate minimum number of units for the amount of time that the dosage will provide enzyme to the mouth, throat, or nasal passage. The concentration of the active units of enzyme believed to provide for an effective amount or dosage of enzyme may be in the range of from about 100 units to about 100,000 units in the environment of the nasal and oral passages. Within that broader range, dosages of from about 100 units to about 10,000 units are believed to be acceptable. Such units can be contained in smaller volumes of carrier such as liquid or saliva, e.g. 1 ml or less (e.g. in the case of a lozenge) or can be contained in larger dosage volumes such as a gargle of several mls. Generally, therefore, larger volumes of carrier will require a greater total number of units to achieve an effective concentration of active enzyme. Hence, acceptable concentrations can be from about 100 units/ml to about 100,000 units/ml of fluid in the environment of the nasal or oral passages. Within this range, concentrations from about 100 units/ml to about 10,000 units/ml are acceptable.

In practice, therefore, the time exposure to the active enzyme units likely will influence the desired concentration of active enzyme units employed in the dosage per ml. For example, carriers that are considered to provide prolonged release (certain nasal sprays, lozenges and encapsulated enzyme) could provide a lower concentration of active enzyme units per ml, but over a longer period of time. Conversely, a shorter duration treatment (e.g., a gargle) could provide a higher concentration of active enzyme units per ml. Any dosage form containing sufficient lysin enzyme to provide effective concentrations of active enzyme at the site of infection or to provide a sufficient prophylactic effect are well within the bounds of routine experimentation and therefore, well within the scope of the instant invention.

Compositions of the instant invention further may comprise at least one other additional agent effective for use in either therapeutic or prophylactic treatment of streptococcal infections or in the alleviation of symptoms thereof. The agent may additionally be effective for some additional therapeutic and/or prophylactic effect, e.g. pain alleviation. Some agents can be topically or systemically active, and can include antibiotics or pain alleviation medications including topical antiseptics, e.g., for sore throat. Alternatively, such agents may be given prior to or after treatment with the instant compositions. Dosages of the antibiotics should be effective for therapeutic or prophylactic treatment of streptococcal infections or for treatment of symptoms of such infections.

While this treatment may be used in any animal or mammalian species, the preferred use of this product is for a human.

Each dose of the lysin containing carrier is kept in contact with the oral mucosa as long as necessary in order to provide the intended therapeutic or prophylactic effect. Administration of the lysin enzyme to the oral mucosa may be by any means such as gargles, mouth rinses, lozenges, troches, chewing gums, candies, powders, and nasal and oral sprays, so long as it is safe and provides the intended prophylactic or therapeutic effect. Skilled artisans may appreciate other possible methods and compositions for delivering the lysin enzyme in accordance with this invention.

EXAMPLE 1

The group C phage lysin enzyme is prepared as follows: Group C streptococcal strain 26RP66 (ATCC #21597) or any other group C streptococcal strain is grown in Todd Hewitt medium at 37 degree(s) C. to an OD of 0.23 at 650 nm in an 18 mm tube. Group C bacteriophage (C1) (ATCC #21597-B1) at a titer of $5\times10^6$ is added at a ratio of 1 part phage to 4 parts cells. The mixture is allowed to remain at 37 degree(s) C. for 18 min at which time the infected cells are poured over ice cubes to reduce the temperature of the solution to below 15 degree(s) C. The infected cells are then harvested in a refrigerated centrifuge and suspended in 1/300th of the original volume in 0.1M phosphate buffer, pH 6.1 containing $5\times10^{-3}$ M dithiotreitol and 10 µg of DNAase. The cells will lyse releasing phage and the lysin enzyme. After centrifugation at 100,000×g for 5 hrs to remove most of the cell debris and phage, the enzyme solution is aliquoted and tested for its ability to lyse Group A Streptococci.

The number of units/ml in a lot of enzyme is determined to be the reciprocal of the highest dilution of enzyme required to reduce the OD650 of a suspension of group A streptococci at an OD of 0.3 to 0.15 in 15 minutes. In a typical preparation of enzyme $4\times10^5$ to $4\times10^6$ units are produced in a single 12 liter batch.

Use of the enzyme requires a minimum number of units of lysin enzyme per test depending on the incubation times required. The enzyme is diluted in a stabilizing buffer containing the appropriate conditions for stability, maximum enzymatic activity. The preferred embodiment is to use a lyophilized lysin enzyme. The stabilizing buffer can comprise a reducing reagent, which can be dithiothreitol in a concentration from 0.001M to 1.0M, preferably 0.005M. The stabilizing buffer can comprise a metal chelating reagent, which can be ethylenediaminetetraacetic acid disodium salt in a concentration from 0.00001M to 1.0M, preferably 0.005M. The stabilizing buffer can comprise a citrate-phosphate buffer in a concentration from 0.001M to 1.0M, preferably 0.05M. The stabilizing buffer can have a pH value in the range of from about 4.0 to 8.0, preferably 6.1. The stabilizing buffer can comprise a bactericidal or bacteriostatic reagent as a preservative. Such preservative can be sodium azide in a concentration from 0.001 percent to 0.1 percent, preferably 0.02 percent.

The preparation of phage stocks for lysin production is the same procedure described above for the infection of phage and group C streptococcus in the preparation of the lysin enzyme. However, instead of pouring the infected cells over ice, the incubation at 37 degree(s) C. is continued for a total of 1 hour to allow lysis and release of the phage and also enzyme in the total volume. In order for the phage to be used for subsequent lysin production the residual enzyme must be inactivated or removed to prevent lysis from without of the group C cells rather than phage infection.

EXAMPLE 2

The enzyme prepared according to example 1 is diluted to a concentration of 100 units/ml in a buffer consisting of 0.05M citrate phosphate buffer pH 6.1 containing 0.1% rabbit immunoglobulin, 0.005M (ethylenedinitrilo) tetraacetic acid disodium salt (EDTA), 0.005M Dithiothreitol, 0.02% sodium azide, 0.01% N-acetylglucosamine. One part colloidal gold sol labelled with Group A Streptococcal Antibody (OD sup 520 1.5) suspended in 0.02M Tris buffer pH 8.2, 1.0% bovine serum albumin, 0.02% sodium azide, 300K units heparin, is added to 3 parts of the enzyme reagent, mixed, filtered through a 0.22 micron filter, and 200 microliters aliquoted per tube and lyophilized. This lyophilized enzyme is stable at elevated temperatures (i.e. 45 degree(s) C.) for short term conditions (i.e. 2 weeks) and long term storage at room temperatures (>1 year).

EXAMPLE 3

Method
1. Start a day culture of group A streptococcal strain S43/192/39R (Streptomycin resistant) (from frozen blood broth); 500 µl in 50 ml of Todd Hewitt (TH) broth containing 1% yeast extract and 100 µl of Streptomycin/ml.
2. Grow to an $OD_{650}$ of 0.59
3. Centrifuge for 15 minutes at 3000 rpm to sediment bacteria.
4. Resuspend organisms in 1 ml volume of TH w/o antibiotics ($3\times10^5$/100 µl as determined by plate count).
5. Add 0.5 of these concentrated cells to ) 0.5 ml of pH 6.1 phosphate buffer as a control.
6. Five minutes before administering to the mice, 0.5 ml of the concentrated cell suspension was mixed with 0.5 ml of phage lysin solution pre-diluted to 10,000 units/ml in pH 6.1 phosphate buffer.

Five mice received 60 µl of "control" solution divided equally orally and intranasally.

Five mice received 60 µl of lysin and bacteria mixture divided equally orally and intranasally.

Throat swabs were performed onto 5% sheep blood, proteose peptone agar plates containing 500 µg/ml of streptomycin. Plates were incubated overnight at 37° C.

The following results were obtained:

|  | 7/22 1d | 7/23 2d | 7/24 3d | 7/28 7d |
|---|---|---|---|---|
|  | Colony Forming Units | | | |
| LYSIN | | | | |
| L1 | 0 | 0 | 0 | 0 |
| L2 | 0 | 0 | 0 | 0 |
| L3 | 0 | 0 | 0 | 0 |
| L4 | 0 | 1 | 0 | 0 |
| L5 | 0 | 0 | 1 | 0 |
| CONTROL | | | | |
| C1 | 26 | 14 | 7 | 0 |
| C2 | >400 | 17 | 100 | 83 |
| C3 | 9 | 0 | 15 | 0 |
| C4 | >400 | >400 | >400 | 220 |
| C5 | 2 | 2 | 30 | 0 |

These results show that the contact between phage lysin and group A streptococci for as little as five minutes prevents the streptococci from colonizing the upper respiratory tract of the mice in this model system.

EXAMPLE 4

To reproduce what might occur when lysin is present in the oral cavity (i.e. through relase by a lozenge) before streptococci enter the environment, animals, bacteria, and lysin were prepared in the same way as described in example 3 (numbers 1–5) except in this experiment, animals were treated as follows:

Lysin: 5 mice received 25 μl of lysin and immediately thereafter they received 50 μl of bacterial suspension.

Control: 5 mice received 25 μl of buffer and immediately thereafter they received 50 μl of bacterial suspension. 24 hrs.

| Lysin | |
|---|---|
| L6 | − |
| L7 | − |
| L8 | − |
| L9 | − |
| L10 | − |
| Control | |
| C6 | − |
| C7 | + |
| C8 | − |
| C9 | + |
| C10 | + |

Result: 0/5 animals containing lysin in their oral cavity when the streptococci were added were colonized, while 3/5 animals that received buffer, then streptococci were colonized. Thus, lysin, if present before group A Streptococci are added, is able to prevent colonization.

EXAMPLE 5

Group A M type 6 streptococci were grown at 37 degrees C overnight in Todd Hewitt media. Organisms were washed once in sterile lysin buffer (50 ml phosphate buffer pH 6.1). The cell pellet was then suspended in 5 ml of the same buffer.

Phage lysin was diluted in lysin buffer containing 5 mM DTT to two times the appropriate units and the mixture was sterile filtered.

1.0 ml of the bacterial suspension was added to 1.0 ml of the appropriate lysin dilution and the mixture was incubated at 37 degrees C. Samples were removed at timed intervals, diluted appropriately and plated on blood agar plates to determine the bacterial count.

Control samples consisted of 1.0 ml of the bacterial suspension added to 1.0 ml of the lysin buffer alone. An aliquot was removed and diluted in 10-fold dilutions and an aliquot plated on blood agar plates to determine the bacterial count.

| | | Results: | | | | | |
|---|---|---|---|---|---|---|---|
| Lysin | Starting | Bacterial counts with lysin | | | | | |
| units | Count | 5 sec | 30 sec | 60 sec | 5 min | 10 min | |
| 1000 | $5 \times 10^6$ | 0 | 0 | 0 | 0 | 0 | (mean 2 exp) |
| 100 | $8.6 \times 10^6$ | 1530 | 1196 | 771 | 64 | 6 | (mean 4 exp) |
| 10 | $9.8 \times 10^6$ | >3000 | >3000 | >3000 | >3000 | >3000 | (mean 3 exp) |

Many modifications and variations of the present invention are possible in light of the above teachings. It is, therefore, to be understood within the scope of the appended claims the invention may be protected otherwise than as specifically described.

What is claimed is:

1. A composition for use in the therapeutic or prophylactic treatment of a Group A streptococcal infection, comprising:
   an effective amount of lysin enzyme produced by Group C streptococcal bacteria infected with a C1 bacteriophage; and
   a carrier for delivering said lysin enzyme to a mouth, throat, or nasal passage of a mammal.

2. The composition according to claim 1, wherein said carrier is selected from the group consisting of candy, chewing gum, lozenge, troche, tablet, powder, aerosol, liquid, liquid spray, nasal spray and nasal ointments.

3. The composition according to claim 1, further comprising a buffer that maintains pH of the composition at a range between about 4.0 and about 9.0.

4. The composition according to claim 3, wherein said buffer maintains the pH of the composition at range between about 5.5 and about 7.5.

5. The composition according to claim 3, wherein said buffer comprising a reducing agent.

6. The composition according to claim 5, wherein said reducing agent is dithiothreitol.

7. The composition according to claim 3, wherein said buffer comprises a metal chelating agent.

8. The composition according to claim 7, wherein said metal chelating agent is ethylenediaminetetraacetic disodium salt.

9. The composition according to claim 3, wherein said buffer is a citrate-phosphate buffer.

10. The composition according to claim 1, further comprising a bactericidal or bacteriostatic agent as a preservative.

11. The composition according to claim 1, wherein said lysine enzyme is lyophilized.

12. The composition according to claim 1, wherein said carrier further comprises a sweetener.

13. The composition according to claim 1, wherein the carrier provides a concentration of from about 100 to about 100,000 active enzyme units per milliliter of fluid in the environment of nasal or oral passages.

14. The composition according to claim 13, wherein said concentration is from about 100 to about 10,000 active enzyme units per milliliter of fluid in the environment of the nasal or oral passages.

15. The composition according to claim 1, wherein said composition is used in the therapeutic treatment of streptococcal infections.

16. The composition according to claim 1, wherein said composition is used in the prophylactic treatment of streptococcal infections.

17. The composition according to claim 15, wherein said streptococcal infection is a streptococcal throat infection.

18. The composition according to claim 1, wherein said carrier is a candy.

19. The composition according to claim 1, wherein said carrier is a chewing gum.

20. The composition according to claim 1, wherein said carrier is a lozenge.

21. The composition according to claim 1, wherein said carrier is a troche.

22. The composition according to claim 1, wherein said carrier is a powder.

23. The composition according to claim 1, wherein said carrier is an aerosol.

24. The composition according to claim 1, wherein said carrier is a liquid spray.

25. The composition according to claim 1, wherein said carrier is a nasal spray.

26. The composition according to claim 1, wherein said mammal is a human.

27. The composition according to claim 1, wherein said carrier is suitable for delivering said lysin enzyme to the mouth and throat.

28. The composition according to claim 1, wherein said carrier is suitable for delivering said lysin enzyme to the nasal passage.

* * * * *